(12) United States Patent
Zhao et al.

(10) Patent No.: US 6,683,934 B1
(45) Date of Patent: Jan. 27, 2004

(54) DUAL ENERGY X-RAY IMAGING SYSTEM AND METHOD FOR RADIOGRAPHY AND MAMMOGRAPHY

(75) Inventors: Jianguo Zhao, Watervliet, NY (US); Beale HibbsOpsahl-Ong, Darien, CT (US); Michael Robert Hopple, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 765 days.

(21) Appl. No.: 09/586,898

(22) Filed: Jun. 5, 2000

(51) Int. Cl.⁷ .................................................. A61B 6/03
(52) U.S. Cl. .................. 378/9; 378/4; 378/5; 378/901; 378/37; 378/98.11
(58) Field of Search ................................ 378/4, 5, 8, 9, 378/16, 18, 37, 62, 98.9, 98.11, 901

(56) References Cited

U.S. PATENT DOCUMENTS

| 4,541,106 A | | 9/1985 | Belanger et al. |
| 4,626,688 A | | 12/1986 | Barnes |
| 4,963,746 A | | 10/1990 | Morgan et al. |
| 5,020,085 A | | 5/1991 | Kawara et al. |
| 5,864,146 A | * | 1/1999 | Karellas .................... 250/581 |
| 6,320,931 B1 | * | 11/2001 | Arnold ........................ 378/56 |
| 2002/0070365 A1 | * | 6/2002 | Karellas .................... 250/581 |

OTHER PUBLICATIONS

Lehmann, L. A. et al., "Generalized Image Combinations in Dual KVP Digital Radiography", *Medical Physics*, Jul./Aug. 1990, pp. 665–675.

Boone, John et al., "Dual-Energy Mammography: A Detector Analysis", *Medical Physics*, Jul./Aug. 1990, pp. 665–675.

Johns, Paul C., et al., "Theoretical Optimization of Dual-energy X-ray Imaging with Application to Mammography", *Medical Physics*, May/Jun. 1985, pp. 289–296.

Niklason, Loren T. et al., "Simulated Pulmonary Nodules: Detection with Dual-Energy Digital Versus Conventional Radiography", *Radiology*, vol. 160, No. 3, Sep. 1986, pp. 589–593.

Fraser, Robert G. et al., "Calcification in Ppulmonary Modules: Detection with Dual-Energy Digital Radiography", *Radiology*, vol. 160, No. 3, Sep. 1986, pp. 595–601.

Johns, Paul C. et al., "Dual-Energy Mammography: Initial Experimental Results", *Medical Physics*, May/Jun. 1985, pp. 297–304.

* cited by examiner

*Primary Examiner*—David V. Bruce
(74) *Attorney, Agent, or Firm*—Donald S. Ingraham; Patrick K. Patnode

(57) ABSTRACT

A digital x-ray imaging system employs a pixelated flat panel digital x-ray detector separated by a space from a source of x-rays which is selectively switchable between first and second, different x-ray energy levels, the space accommodating a body to be subjected to x-ray irradiation and imaging. A computer controls the x-ray source to irradiate the body with the first and second energy level x-rays and produce corresponding first and second x-ray images respectively of the first and second energy levels on the detector, the computer processing the respective digital signal outputs of the detector for the first and second digital images respectively of the first and second energy levels for each pixel, in individual succession for all pixels, and selectively produces and displays a soft tissue image or a bone/calcification image.

64 Claims, 5 Drawing Sheets

*fig. 6A* Material Decomposition

*fig. 5A* Subtraction

"Normal" single energy x-ray image at 110 kvp

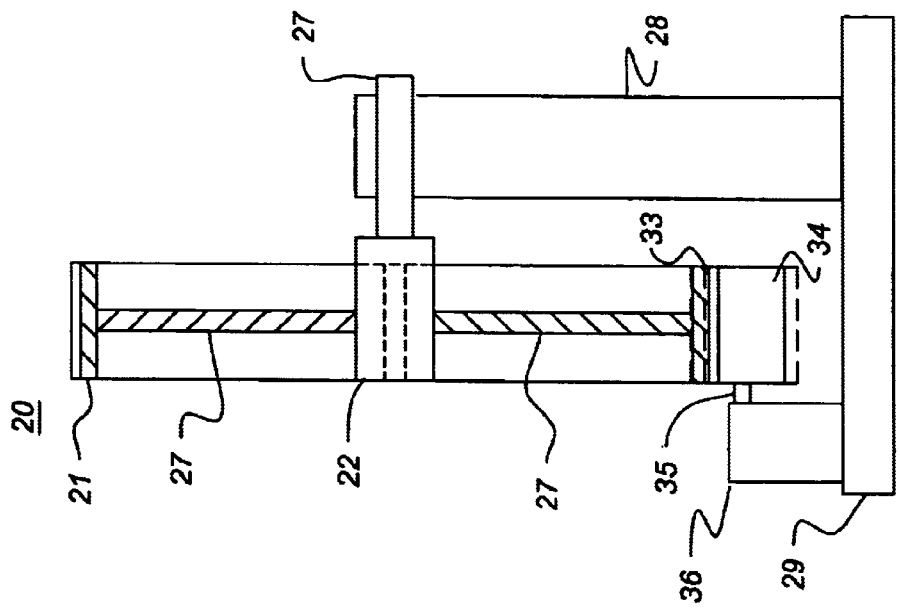
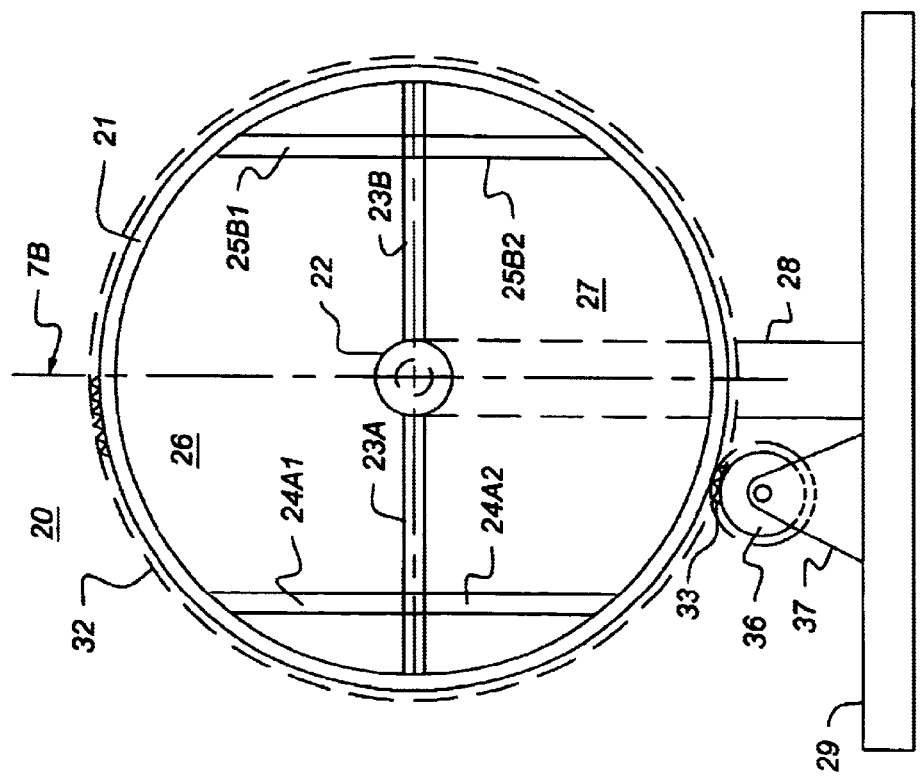

DUAL ENERGY X-RAY IMAGING SYSTEM AND METHOD FOR RADIOGRAPHY AND MAMMOGRAPHY

BACKGROUND OF THE INVENTION

This invention relates to a digital x-ray imaging method and system for producing soft tissue images and bone/calcification images for radiography and mammography and, more particularly, to such a digital x-ray system employing dual (i.e., two different) x-ray energies, obtained by rapidly switching an x-ray energy source between low and high energy levels, and using a single large area pixelated digital x-ray detector to capture the resulting and respective, dual energy x-ray images. The dual energy images are processed, with a pre-calibrated database and adjustable parameters, to produce respective, and separate, soft tissue images and bone/calcification images, affording enhanced visibility of any nodules or clusters of calcification, facilitating earlier detection of lung and/or breast cancers.

In "normal" projection x-ray radiographic and mammographic images, nodules or clusters of calcifications can be obscured by structured noise/background, i.e., signal noise in the detected x-ray image caused by irradiation of bone structure (e.g., ribs or spine) or by contrast effects from, e.g., glandular and fatty tissues. In an effort to reduce such noise/background, dual energy x-ray imaging has been explored extensively, with both film/cassette systems and also digital systems.

Most of the early work in this field was based on film/cassette systems and, of necessity, employed a single x-ray energy spectrum and dual detectors. Particularly, with film/cassette systems, rapidly switching between high and low levels of x-ray energy (kVP) and using a single film/cassette for each image is not technologically feasible. Further, the limited dynamic range and lower detective quantum efficiency (DQE) of film/cassette systems preclude any such dual energy applications. The images obtained, moreover, were not acceptable.

Digital systems employing dual energy x-ray imaging offered at least the potential of improved images; however, there is a need in such systems of an increased separation of high and low X-ray energy levels yielding a practical, effective and efficient system performing dual energy X-ray imaging.

BRIEF SUMMARY OF THE INVENTION

The present invention utilizes a dual energy x-ray digital imaging system that includes an x-ray generator capable of switching from high energy to low energy rapidly (e.g., on the order of ms), a single, pixelated digital x-ray detector, a computer, a display unit and related software to acquire and process the high and low energy x-ray images for display.

BRIEF DESCRIPTION OF THE DRAWINGS

FIGS. 5A and 5B are photographic reproductions of bone and soft-tissue images of phantoms, respectively, produced by use of a dual energy digital x-ray imaging apparatus and subtraction processing in accordance with the invention;

FIGS. 6A and 6B are photographic reproductions of bone and soft-tissue images of phantoms, respectively, produced by use of a dual energy digital x-ray imaging apparatus and material decomposition processing, in accordance with the invention; and FIGS. 7A and 7B are front and side elevational views of external filtration used in the FIG. 1 system, FIG. 7B being taken along a line 7B—7B in FIG. 7A.

DETAILED DESCRIPTION OF THE INVENTION

Figure 1:
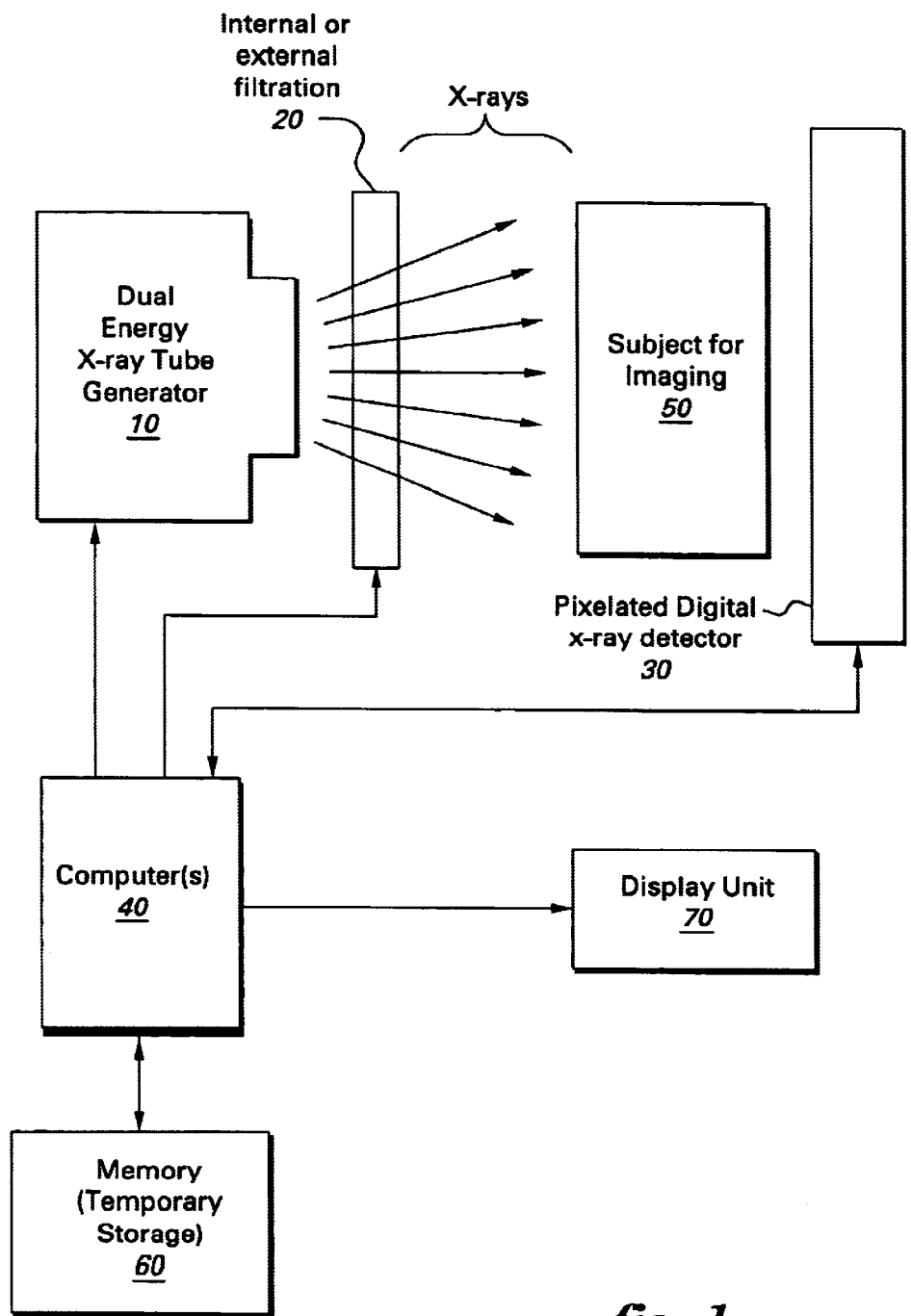
FIG. 1 is a block diagram of a dual energy x-ray imaging system for radiography and mammography in accordance with a first embodiment of the invention.

The dominant reaction mechanisms of x-ray interaction with a material (e.g., a patient's body), in the energy ranges relevant to radiography and mammography, are photoelectric ionization and Compton scattering (i.e., Coherent or Rayleigh scattering is small). The x-ray attenuation can be expressed as:

$$I = I_0 e^{-\mu t}, \tag{1}$$

wherein:

I is the resultant x-ray intensity, after transmission through the irradiated/attenuation material(s), as seen at the detector;

$I_0$ is the incoming x-ray intensity; and t and $\mu$ are the thickness and the attenuation coefficient, respectively, of the attenuation material(s);

Moreover, the attenuation coefficient $\mu$ is a function of both the x-ray energy and the nuclear charge (Z) of the attenuation material(s) and, as noted above, $\mu$ can be further decomposed into:

a. a Compton scattering component: f1(Ex)g1(Z); and b. a photoelectric ionization component: f2(Ex)g2(Z), wherein:
   i) f1, f2, g1 and g2 are different functions,
   ii) Ex is the x-ray energy,
   iii) f(Ex) is only dependent on the x-ray energy,
   iv) (Z) is the nuclear charge of the attenuation material (e.g., a body part or chest phantom), and
   v) g(Z) is only dependent on the nuclear charge of the material;

This implies that the attenuation of any material can be decomposed into two known materials, with equivalent thicknesses, if the attenuation can be approximated by Compton scattering and photo-electric effect. Any two known materials can form a two dimensional material base and any other material can be expressed as a vector in that material base plane. Therefore, materials can become "look-alikes" under rotations of certain angles or projection to a particular axis. Nevertheless, while any two known materials can be chosen, Lucite and Aluminum are preferred because of their proximity to mammal tissue and bones, respectively, with the result that the corresponding coefficients are close to unity. In principle, the coefficients may vary significantly and even be negative.

The dual energy x-ray imaging system and method of the invention implements the above reaction mechanism in a practical, effective and efficient manner. More particularly, the embodiment of the invention shown in FIG. 1 comprises an x-ray tube/generator 10 which is capable of switching high voltage (kVP and, therefore, x-ray energy) quickly (e.g., at a 1 ms rate), filtration 20 which may comprise internal and/or external filters, a single flat-panel digital pixelated x-ray detector 30 and a computer 40, which controls the x-ray tube/generator 10 and the x-ray detector 30 so as to acquire dual energy x-ray images of a subject 50, located in the space between the x-ray tube/generator 10 and the detector 30 and proximate to the detector 30. The dual energy x-ray images, one at a low kVP and the other at a high kVP, are acquired automatically, in rapid succession, and are stored in temporary storage 60 for further processing by the same (or another) computer 40 and for display on the display unit 70. As is well known, respective and different x-ray systems typically are employed in radiography and mammography, differing in their geometries and the positioning of the patient relatively thereto, in their energy levels, and the like. The present invention is applicable to both such systems; moreover, the invention is not limited, as to its imaging capabilities, to medical applications although they constitute the presently preferred embodiment, or embodiments, of the invention.

For radiography, the low and high energies of x-rays typically are selected by appropriate settings of the x-ray tube controls (not shown), e.g., to a 50–70 kVP range for low energy imaging and a 110–140 kVP range for high energy imaging, and thus with a maximum x-ray energy of 70 keV for the lower x-ray energy spectrum and of 140 keV for the higher x-ray energy spectrum. A suitable state of the art system for implementing the present invention for radiography is the Revolution™ XQ/i Digital Chest Imaging System produced and sold by the G.E. Medical Systems division of the assignee hereof.

For mammography, the typical dual ranges of x-ray settings are a 20–30 kVP range for low energy and a 40–70 kVP range for high energy, and thus with a corresponding maximum x-ray energy of 30 kVP for the lower x-ray energy spectrum and a maximum of 70 kVP for the higher x-ray energy spectrum. A suitable state of the art system for implementing the present invention for mammography is the Senographe 2000D™ Fully Digital Mammography System produced and sold by the G.E. Medical Systems division of the assignee hereof.

Further, as is well known and in both radiography and mammography, an appropriate set of low/high energy x-ray settings is chosen for imaging of a given subject, taking into account, e.g. patient size.

The flat panel, large area digital x-ray detector 30, which may be the Revolution™ flat panel digital detector, employed in both the Revolution™ XQ/i and Senographe 2000D digital systems, is set to normal data acquisition status and thus in a ready state for acquiring images, the same as for conventional, or normal, single energy radiography or mammography images. However, in accordance with the present invention, the system is configured to acquire two images in an automatic sequence and in rapid succession. The imaging sequence is programmed, at the beginning, in the computer 40: e.g., select the high kVP and low kVP levels, select respective exposure levels of the two images (i.e., respective mAs for the high and low kVPs) and select different x-ray filters (either or both of internal and external, if desired). The high and low kVP (energies) are selected to be spaced well apart, or separated, from each other, as noted above. The exposure times (duration) are minimized by choosing a maximum, but safe, output power of the x-ray tube and high voltage (energy) setting, for both low and high energy images.

More particularly, the x-ray exposure time is minimized by considering the maximum safe output power of the x-ray generator and the desired x-ray energy (kVP). This affords a determination of the maximum safe current and, correspondingly, the shortest x-ray pulse length for a desired x-ray energy level and dose. The exposure level ("mAs") is normally defined as the product of the electric current (mA) in the x-ray tube and the time duration(s) (in seconds) ("s") of exposure, i.e., mili-Amper-second. When a certain exposure level (mAs) is selected, the computer automatically chooses a certain current (mA) and exposes the patient for the corresponding duration ("s"). When designing such automatic settings, one can consider the maximum safe output power and the kvp being used, since that determines the current mA in accordance with the relationship:

$$\text{max\_safe\_power} = \text{selected\_voltage(kvp)} \times \text{current (mA)} \quad (2)$$

Once the current "mA" is selected, the exposure duration "s" is determined by the selected exposure level mAs.

For example, 70 kvp and 140 kvp may be employed as the low and high energy x-rays for dual energy radiography. If exposure levels of 25 mAs for 70 kvp and 2 mAs for 140 kvp are required, using Equation 2, one can select the respective maximum safe current for each of the low and the high energy x-rays. The respective, required durations ("s") for the low and the high energy x-rays therefore are minimized by selecting the maximum safe current (mA).

Since higher energy x-rays more easily penetrate a body, irradiated thereby, than do lower energy x-rays, the image contrast is lower with higher energy x-rays because the detector is more uniformly exposed by the higher energy x-rays, as between regions of the detector covered by the body and remaining, uncovered regions which are exposed directly to the "raw" x-rays. Thus, for the higher energy x-rays, the number of counts (signals) in the covered detector region behind the body will be closer to the number of counts (signals) in the uncovered detector region exposed to the raw x-rays. In other words, since high energy x-rays more easily penetrate the body, they are attenuated only by a relatively small amount (i.e., relative to attenuation of relatively lower energy x-rays), resulting in a more uniform signal level in the detector, as between the image area and the exposed areas. As a corollary, the lower energy x-rays are attenuated more greatly in the body than the high energy x-rays; thus, in order to get sufficient x-rays passing through the patient to produce detection signals of adequate strength, more low energy x-rays are required; the increased amount of low energy x-rays, for a region not covered by the imaging object and which region is thus exposed to raw x-rays, can over-expose the detector. For this reason, the higher energy x-ray image is acquired first, since having a lesser residual effect on the detector relatively to the lower energy x-ray image.

For radiography, the internal and/or external filters can be switched for the respective, high energy and low energy x-ray images to improve the x-ray spectra and, therefore, the image quality; one may use, e.g., a 0.25 mm Cu filter for a high energy image and a 2 mm Al filter for a low energy image. While the foregoing provides an illustrative example of specific such switchable copper and aluminum filters, in practice, these elements will have values over a range of differing thicknesses and the appropriate thickness range which is selected, for each filter, will depend on the patient size, the actual x-ray energy, the x-ray tube output, the detector which is used and other factors, as are conventionally understood. Likewise, for mammography, other filters can be used depending on the x-ray tube anode materials, and may be of representative materials such as Rh, Mo, etc. Again, the particular size or thickness will be determined in conventional fashion, based on the same factors, as mentioned above for purposes of radiography but as applied to the typically very different attenuation characteristics and size of the object to be imaged for purposes of mammography.

For x-ray imaging as defined in Equation (1) above, the logarithm of the ratio of the x-ray transmission intensity (I) through a body to the corresponding (raw) x-ray intensity ($I_0$), at each pixel on the detector, is the total attenuation of the body at the pixel, viz.:

$$\log(I/I_0) = \mu_i t_i,\qquad(3)$$

wherein:

i is a pixel number; and $\mu_i$ and $t_i$ are the attenuation coefficient and the thickness, respectively, of the imaging body at the ith pixel.

The above term "total attenuation" is intended to include the individual attenuation contributions of all materials in the body (which may include one or more of bone, soft tissue, and tumors) along a line extending from the x-ray tube to an individual pixel on the detector, and wherein the line effectively represents the component of the x-ray energy emitted by the x-ray tube which corresponds to and would be detected by the individual pixel as a raw beam (i.e., in the absence of any body therebetween).

In accordance with a decomposition processing embodiment of the invention, the total attenuation at each pixel, $\mu_i \cdot t_i$, as derived from the image data from the detector, is decomposed into equivalent thicknesses respectively of two chosen materials, i.e., an equivalent attenuation of a phantom body comprising a combination of selected, respective thicknesses of two different, chosen phantom materials, e.g., Lucite and aluminum, using a predetermined calibration table/function. An Aluminum image and a Lucite image then are formed. With adjustable weightings for the Aluminum image and the Lucite image, separated soft tissue images and bone/calcification images are obtained.

To establish the predetermined calibration table/function, or database, two calibration phantoms preferably are made, respectively of Lucite and Aluminum; however, the invention is not limited thereto and, instead, the phantoms may be made of any two different materials, each with a known density and equivalent Z. Preferably, as shown in the exploded view of FIG. 2, the phantoms are configured as a pair of stepped elements, element 100 (e.g., aluminum) and element 200 (e.g., Lucite) respectively having steps 100-1 through 100-n and 200-1 through 200-n. In each phantom, successive steps are in parallel relationship and incrementally increase in thickness in a direction from the thinnest (100-1 and 200-1) and toward the thickest (100-n and 200-n) steps. The lateral dimensions (i.e., length and width) of the pair of phantoms 100 and 200 are substantially the same, facilitating the assembly of the two in orthogonal and stacked relationship, typically with the thicker phantom 200 disposed on the thinner phantom 100 and maintained in position directly at the surface of the screen of the detector 30 (see FIG. 1). Further, the two phantoms should be positioned or fabricated, relative to each other, such that each material has a step of zero thickness matching the full range of steps of the other material. Those steps of thicknesses of only the other (i.e., single) phantom material can be imaged at the same time and provide calibration data for all step thicknesses, exclusively of the other phantom material.

The assembled phantoms are placed on the detector and irradiated by x-rays from the x-ray tube generator 10 (FIG. 1) and counts of the attenuated x-rays at each pixel are obtained from the pixelated digital x-ray detector 30, at each of the low and high energy level x-rays, for as many of the discrete thickness ratios of the aluminum and the Lucite phantoms, as are desired. Thus, a related set of the calibration phantoms 100 and 200 are placed in front of the detector 30 (FIG. 1) and high and low energy level x-ray images are taken and digital signals (numbers of counts) at each pixel and corresponding to the known, different combinations of respective thicknesses of the Lucite and aluminum phantoms are obtained and assembled in a calibration table. Moreover, within each set, intermediate values, to the precision required, may be computed. The calibration table thus consists of the numbers of counts, respectively at high and low energy x-rays (h, l), for the successive steps and corresponding thicknesses of Lucite and Aluminum ($t_{Lucite}$, $t_{Aluminum}$), which table is stored in memory 60 (FIG. 1) for later use.

Dual object images (with counts at each pixel), respectively at high and low x-ray energies, are then decomposed on a pixel-by-pixel basis into Lucite and Aluminum equivalent thicknesses using the calibration table stored in memory 60, the computer 40 and a search/fit algorithm. The two closest sets of (h, l) counts then are found from the calibration table, and a multi-parameter interpolation is performed to determine the equivalent thicknesses of aluminum (Al) and Lucite for each pixel (i). This can be expressed as:

$$\mu_i \cdot t_i = a_i(\text{Al}) \cdot \mu_{Al} + b_i(\text{Lucite}) \cdot \mu_{LUC} \qquad(4)$$

wherein:

$t_i$ is the thickness of the object corresponding to the particular pixel (i) in consideration;

$a_i$ and $b_i$ are the equivalent thicknesses of Lucite and Aluminum, respectively; and the corresponding $\mu$'s are the attenuation coefficients.

As will be understood, equation (4) is solved twice, using the respective data from the low and high-energy x-ray images, thereby to determine the respective equivalent thicknesses of aluminum and Lucite, corresponding to the irradiated body image, at each pixel.

Once the respective equivalent thicknesses of Aluminum and Lucite are found, using adjustable parameters φ, soft tissue images and bone/calcification images can be obtained from the relationship:

$$A_i(\phi) = a_i(\text{Al}) \cdot \sin\phi + b_i(\text{Lucite}) \cdot \cos\phi \qquad(5)$$

The parameter φ is determined experimentally, and functions to cause the otherwise observed structural background, e.g., ribs/spine, to disappear, producing a desired anatomy (soft tissue) image, or, alternatively, to cause the otherwise observed anatomy (soft tissue) image to disappear, producing a desired bone/calcification image. $A_i(\phi)$ thus can be displayed on a display unit.

Figure 3:
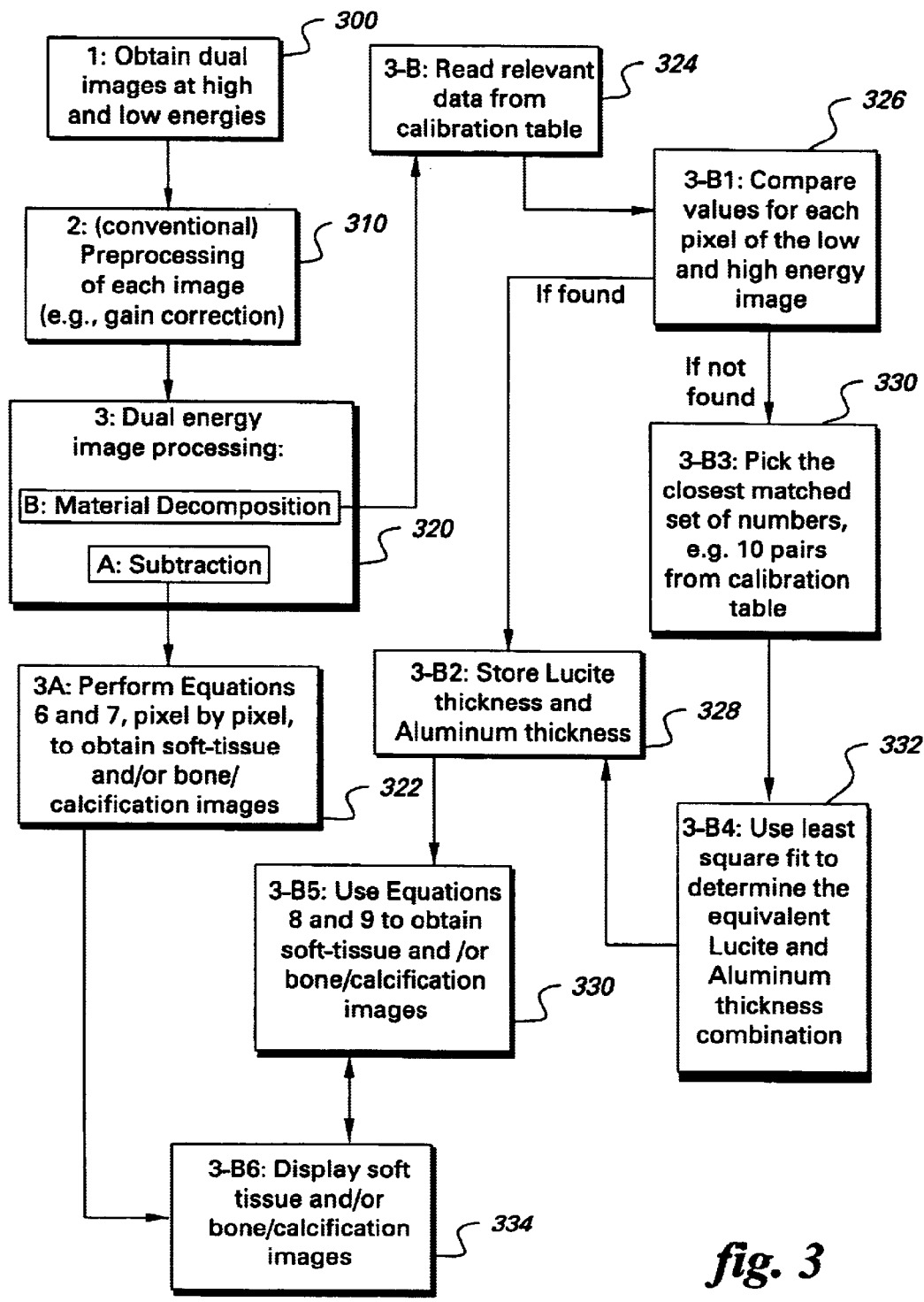
FIG. 3 is a flow chart of the operation of the system of FIG. 1 for developing separated soft-tissue and/or bone/calcification images for display.

In accordance with a subtraction processing embodiment of the invention, discussed more fully in connection with FIG. 3 at step 3A, phantoms are not employed and, instead, the dual energy level images are processed based on the number of counts per pixel, for the low and high energy level images, after conversion of the number of electrons to digital regions and then adjusted by empirically determine weighting factors for selectively producing a soft tissue image (i.e., for mammography) or a bone/calcification image (e.g., for radiology).

FIG. 3 is a flow chart of the operation of the system of the invention, employing the preestablished data from the calibration table/database, and wherein:

STEP 1 (300): The images are acquired automatically after initialization of the sequence, by the computer, e.g., first, take a high energy x-ray image, automatically and quickly switch the x-ray tube to a low energy setting, in as short a time as possible, while affording sufficient time (e.g., a maximum of 100 ms) to acquire the first image from the detector and store same in temporary storage and to prepare for taking the second image. The desire of the short time interval is to minimize the likelihood and potential extent of movement of the body part relative to the sensor, between the two images. The different x-ray filters (e.g., thin aluminum) can be switched automatically, once selected and programmed.

STEP 2 (310): The images are processed by further computer processing of the image data. The images of the two image set are processed first, individually, as is any normal or conventional single energy x-ray image for detector gain corrections with gain correction images (e.g., for non-uniformity of detector and x-ray distribution).

STEP 3 (320): The corrected images are then processed as a set of dual energy images to obtain soft tissue and bone images for radiography and soft tissue and calcification images for mammography. A choice is made in step between subtraction processing (A) and material decomposition processing, shown respectively as alternative steps 3-A (322) and 3-B (324), in FIG. 3; conversely, the two alternatives both may be performed, to permit comparison of the respective results.

STEP 3-A (322): In the subtraction processing method, the dual images are processed, pixel by pixel (in number of counts per pixel, after converting the number of electrons to digital signals), as follows, to obtain resulting dual energy images(for radiography or mammography):

$$\text{(Soft-tissue image)}_i = [(L_i)/(H_i)^{w(soft)}] \quad (6)$$

$$\text{(Bone/calcification)}_i = [(L_i)/(H_i)^{w(bone)}] \quad (7)$$

where "i" denotes the ith pixel on the flat panel x-ray detector, the procedure being performed, in individual succession, for all pixels. Li and Hi are the pixel values (number of counts, per pixel, after conversion of the number of electrons to digital signals) of the ith pixel for the low and high energy x-ray images, respectively, and the indicated ratio of same (i.e., $(L_i)(H_i)$) is logarithm subtractions (hereinafter, "subtraction"). Further, w(soft) is the weighting factor to obtain a soft-tissue image and w(bone) is the weighting factor to obtain a bone/calcification image, for radiography and mammography, respectively. The weighting factors may be determined empirically by observing the quality of resulting images, e.g., for soft-tissue images, the weighting factor is adjusted until bone structure disappears in the resulting soft-tissue image and, similarly, is adjusted to make the soft-tissue disappear for producing a resulting bone/calcification image. Thus, the exponent "w(soft)" is selected so as to cause the bone structure to disappear in the resulting soft tissue/anatomy image and the exponent "w(bone)" is selected so as to cause the soft tissue/anatomy structure to disappear in the resulting bone image. The weighting factors are the same for all pixels, for each set of the dual energy images.

STEP 3-B (324): The second method of processing image is called "material decomposition." At step 3-B, the corrected dual energy images are processed, by using data from pre-determined calibration tables which consist of correlated information of Lucite thickness, Aluminum thickness, a series of x-ray energies, different x-ray filtration (both internal and external) and exposure levels for low and high energies and the number of counts for each of these combinations.

For radiography, the Lucite step phantom 200 may be of a thickness range of 0–30 cm in fine steps of, e.g., 5 mm or finer, and the Aluminum step phantom 100 may be of a thickness range of 0–2 cm, in fine steps of, e.g., 0.5 mm or finer. For mammography, the Lucite step phantom 200 can be of 0–10 cm, in 2 mm steps or finer, and the Aluminum step phantom 100 may be of 0–5 mm, in 0.2 mm steps or finer. The maximum thickness and step size are examples, only, and a final selection should be determined by the thickness of a potential subject and a necessary resolution as is required for the imaging system.

The two phantoms 100 and 200 are placed orthogonally with respect to each other in front of the x-ray detector 20 and different combinations of respective thicknesses of Lucite and Aluminum are "seen" by the x-ray tube and the detector. Images are taken at different, switched x-ray energy level settings; preferably, this is done with respectively different, switched x-ray filtrations. The resulting images are gain corrected, as for a "normal" x-ray imaging process, for detector response and x-ray intensity distribution, over all the different regions (i.e., over the entire sensing surface) of the pixelated x-ray detector 30. The resulting images have a number of counts for different combinations of Lucite and Aluminum thicknesses and different kVP, filtration and exposure levels. This information is recorded and stored in the calibration table for later search/use.

As an alternative to the empirical approach of developing data for calibration tables pursuant to the use of phantoms, supra, calibration tables having the same values may be obtained by simulations and calculations based on a knowledge of the x-ray spectra at both the high and low voltage settings, x-ray tube output characteristics, the filtration which is employed, the known attenuation properties of Lucite and Aluminum and the detector response characteristics. It is also possible to use a combination of both empirical measurements and simulations, or to obtain calibration data at arbitrary x-ray tube high voltage settings, filtration, exposure level, Lucite and Aluminum thickness.

For each set of dual energy images of an imaging subject, the total attenuation at each pixel location can then be decomposed into a combined Lucite and Aluminum thickness using the pixel values (for low and high x-ray energies) and the calibration table at step 3B-1 (326). A computer program is used to decompose the dual energy images of the subject, at each pixel, into the equivalent combination of Lucite and Aluminum thicknesses. The computer program controls the computer 40 to read the related data (for the high voltages, filtration, mAs) from the calibration table. For each pixel of the object image, the corresponding counts at high and low kVPs are compared with the calibration table data to find the best match, as to the number of counts under the same conditions, at step 3B-1.

If "exact" matches (within predefined resolutions) are found for a number of counts at both low and high energies, the corresponding Lucite and Aluminum thickness is accepted as the equivalent attenuation of the subject at the pixel location, at step 3B-2 (328). This procedure continues, in succession, for all the pixels of the x-ray detector.

If no "exact" matches are found at step 3-B1, the closest sets of count numbers for both low and high energies (e.g., using 10 sets of numbers) are determined and, then, a least-square fitting procedure is used to obtain the equivalent, respective thicknesses of Lucite and Aluminum at each pixel at steps 3-B3 (330) and 3-B4 (332), respectively, and the result is stored at step 3-B5 (330).

Once all the pixel values are decomposed into equivalent combinations of Lucite and Aluminum thicknesses, a Lucite image and a Aluminum image are obtained, with each pixel corresponding to the deduced thickness of the corresponding material (i.e., Lucite or Aluminum). By recombining these two images (i.e., the Lucite and Aluminum images), a soft tissue image and a bone, or calcification, image can be obtained by rotation in a material base of Lucite and Aluminum, at step 3-B5:

$$(\text{Soft-tissue})_i = [b_i(\text{Lucite})_i \cdot \cos(\phi_s) + a_i(\text{Aluminum})_i \cdot \sin((\phi_s)] \quad (8)$$

$$(\text{bone/calcification})_i = [b_i(\text{Lucite})_i \cdot \cos(\phi_b) + a_i(\text{Aluminum})_i \cdot \sin((\phi_b)] \quad (9)$$

where:
i is the ith pixel,
(Lucite)$_i$ and (Aluminum)$_i$ are equivalent Lucite and Aluminum thicknesses at the ith pixel from the decomposed image; and
$\phi_s$ and $\phi_b$ are predefined rotation angles to obtain, respectively, a soft-tissue image and a bone, or calcification, image;

The resulting images (soft-tissue or bone/calcification) are sent to the display unit 70 for display and/or to storage device 60 for storage therein, at step 3-B6 (334).

Figure 4:
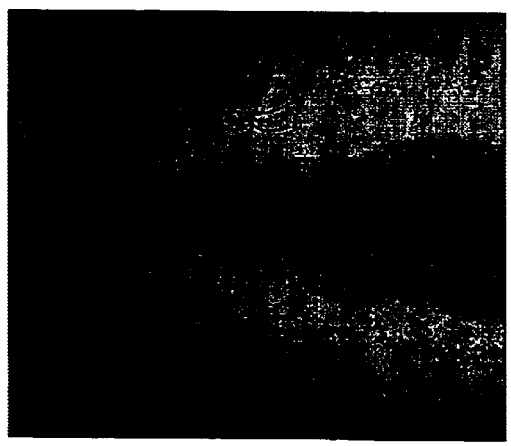
FIG. 4 is photographic reproduction of a conventional single energy x-ray image of a simulated body part (i.e., a human chest phantom) and comprising a body with handwritten annotations "R" and "L", written on and indicating the right and left halves of the chest phantom, and which are reproduced in the actual image.

FIG. 4 is a photographic reproduction of a fully processed and displayed image of a chest model phantom, produced by a conventional, single energy x-ray imaging system at 110 kVP.

Figure 5B:
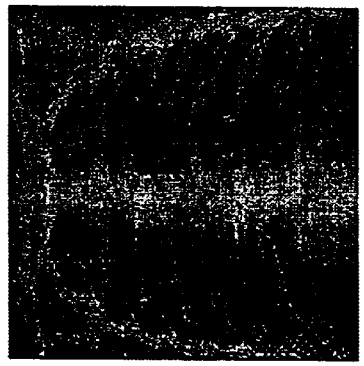
Figure 5B:
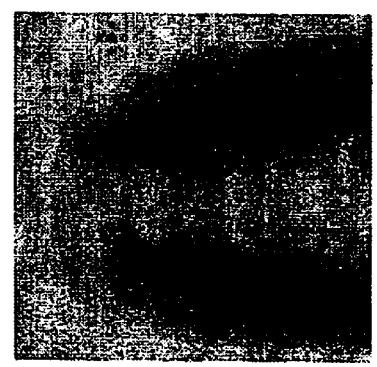

FIGS. 5A and 5B, respectively, are photographic reproductions of fully processed and displayed bone-image and soft-tissue images of the same chest model phantom as in FIG. 4, produced by a dual energy digital x-ray imaging system and subtraction processing in accordance with the present invention.

Figure 6B:
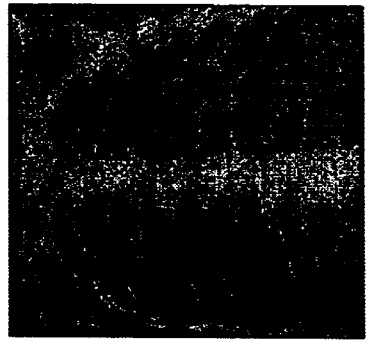
Figure 6B:
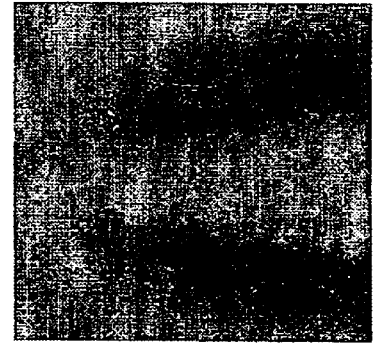

FIGS. 6A and 6B, respectively, are photographic reproductions of fully processed and displayed bone-image and soft-tissue images of the same chest model phantom as in FIG. 4, produced by material decomposition processing in accordance with the present invention.

Figure 2:
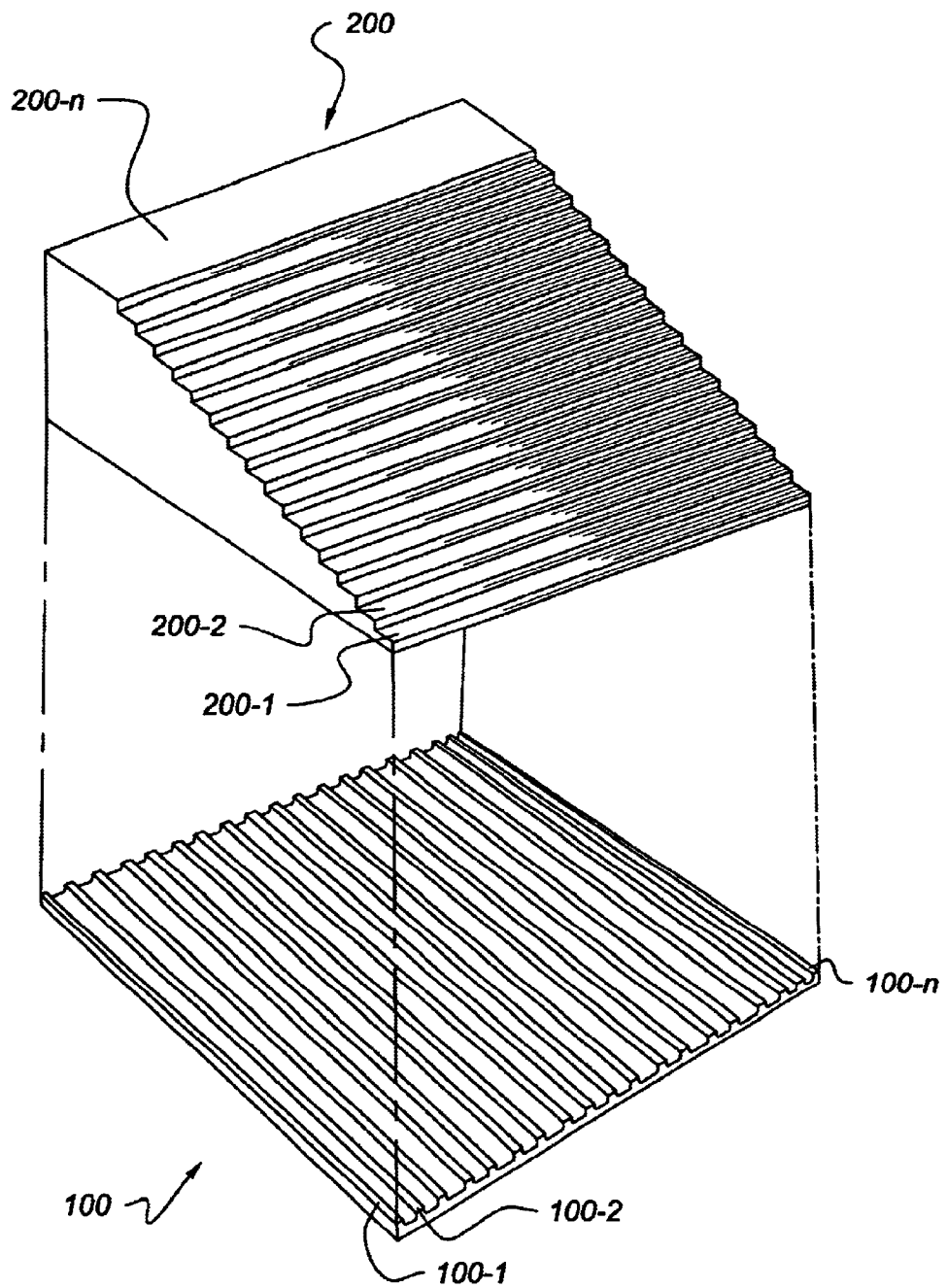
FIG. 2 is a schematic, perspective view of a pair of phantoms employed in the system of FIG. 1 for developing a calibration table.

FIGS. 7A and 7B are front and side elevational views (FIG. 7B being partly in cross-section) of external filtration 20 of FIG. 1. Filtration 20 may comprise a circular, or circumferential, frame 21 with a central hub 22 having radial spokes 23A and 23B and respective transverse supports 24A1 and 24A2, and 25B1 and 25B2 extending to and interconnected with the circular frame 21 and defining corresponding openings for a pair of complementary filtration elements (i.e., first and second filters) 26 and 27, each of a planar and substantially semi-circular configuration, fitted about its perimeter edges to the respective frame supports. Hub 22 has a mounting shaft 27 received for rotation in a support 28 secured to a base 29.

The circumferential support 21 has teeth 32 extending about the outer circumferential surface thereof and which engage teeth 33 of a gear 34 mounted on a drive shaft 35 of a motor 36, in turn, supported by bracket 37 on the support base 29.

The motor 36 is driven by a timing control from the computer 4 over a control line so as to be synchronized with the switching between the first and second, different x-ray energy levels output by the x-ray generator 1, and such that the unobstructed one of the two filters 26 and 27 (i.e., at the upper most position in FIGS. 7A and 7B) is in the line of travel of the x-ray beams from the generator 1 to the subject being imaged and the pixelated x-ray detector 30. Thus, by synchronizing the rotation and corresponding alternating positions of the two different filter elements 26 and 27 with the switching of the generator 10 between the high and low power levels, respectively, optimum imaging conditions are achieved for producing the first and second x-ray images respectively of the first and second, different, energy levels on the detector 30.

The invention has been described hereinabove with reference to one or more preferred embodiments. However, the invention is not limited thereto and, instead, the claims should be entitled to their broadest and fullest interpretation consistent with the disclosure herein. Accordingly, numerous modifications and adaptations of the invention will be apparent to those of skill in the art and, it is intended by the appended claims to cover all such adaptations and modifications as fall within the true spirit and scope of the appended claims.

What is claimed is:

1. A digital x-ray imaging system, comprising:
   a pixelated flat panel digital x-ray detector separated by a space from a source of x-rays selectively switchable between first and second, different x-ray energy levels, the space accommodating a body to be subjected to x-ray irradiation and imaging;
   a computer controlling the x-ray source to irradiate the body with the first and second energy level x-rays and produce corresponding first and second x-ray images respectively of the first and second, different energy levels on the detector, the computer processing the respective digital signal outputs of the detector for the first and second digital images respectively of the first and second, different, energy levels for each pixel of the pixelated flat panel digital x-ray detector and selectively producing and displaying a soft tissue image and a bone/calcification image.

2. A digital x-ray imaging system as recited in claim 1, further comprising:
   first and second, different filters selectively switched so as to be disposed between the source and the space accommodating a body, independently and respectively, for the first and second, different x-ray energy levels.

3. A digital x-ray imaging system as recited in claim 1, wherein:
   for radiography, the first x-ray energy level is selected in a range of 50–70 kVP for low energy imaging and the second, different, x-ray energy level is selected in a range of 110–140 kVP for high energy imaging.

4. A digital x-ray imaging system as recited in claim 3, further comprising:
   first and second, different filters selectively switched so as to be disposed between the source and the space accommodating a body, independently and respectively, for the first and second, different x-ray energy levels.

5. A digital x-ray imaging system as recited in claim 4, wherein:
   the first filter comprises an approximately 2 mm aluminum filter and the second filter comprises an approximately 0.25 mm Cu filter, the actual values being selected within a range of differing thicknesses as a function of patient size, x-ray energy and x-ray tube output.

6. A digital x-ray imaging system as recited in claim 4, wherein the computer determines a minimum exposure time for a selected maximum safe output power of the x-ray generator and a desired x-ray energy (kVP) by:
   determining the current (ma) in accordance with:

$$\text{max\_safe\_power} = \text{selected\_voltage(kv)} \times \text{current(mA)};$$

and
setting the exposure time(s) in accordance with a selected exposure level (mAs).

7. A digital x-ray imaging system as recited in claim 1, wherein:
for mammography, the first x-ray energy level is selected in a range of 20–30 kVP for low energy imaging and the second, different, x-ray energy level is selected in a range of 40–70 kVP for high energy imaging.

8. A digital x-ray imaging system as recited in claim 7, further comprising:
first and second, different, filters selectively switched respectively for the first and second, different x-ray energy levels, disposed between the source and the space accommodating a body.

9. A digital x-ray imaging system as recited in claim 8, wherein:
the first filter comprises an approximately 2 mm aluminum filter and the second filter comprises an approximately 0.25 mm Cu filter, the actual values being selected within a range of differing thicknesses as a function as patient size, x-ray energy and x-ray tube output.

10. A digital x-ray imaging system as recited in claim 8, wherein:
the computer determines a minimum exposure time(s) for a selected maximum safe output power of the x-ray generator and a desired x-ray energy (kVP) by determining the current (ma) in accordance with:

max_safe_power=selected_voltage(kv)×current(mA)

and setting the exposure time(s) in accordance with a selected exposure level MAs.

11. A digital x-ray imaging system as recited in claim 1, wherein the computer processing comprises a selected one of subtractive processing and material decomposition processing.

12. A digital x-ray imaging system as recited in claim 11, wherein the computer performs subtraction processing in accordance with:
defining a number of counts representing the energy level of the x-ray image detected by each pixel of the detector, for all pixels of the detector and for each of the first and second x-ray energy level images;
subtracting the respective counts at each pixel, corresponding to the first and second, different x-ray energy level images, for all pixels and
providing a first adjustable weighting factor to obtain a soft-tissue image and a second adjustable weighting factor to obtain a bone/calcification image and responding to selective adjustment of the first and second weighting factors, respectively for radiography and mammography, to cause the bone structure to disappear in a resulting soft-tissue image and, alternatively, to cause the soft-tissue to disappear in a resulting bone/calcification image.

13. A digital x-ray imaging system as recited claim 1, wherein:
the computer performs subtraction processing in accordance with:

(Soft-tissue image)$_i = (L_i)/(H_i)^{w(soft)}$ (Bone/calcification)$_i = (L_i)/(H_i)^{w(bone)}$ wherein:
"i" denotes the ith pixel on the pixelated flat panel digital x-ray detector,
Li and Hi represent numbers of counts corresponding to the digital signals output by the detector for the first and second energy level x-rays, respectively, for the ith pixel; and
w(soft) is an adjustable weighting factor to obtain a soft-tissue image and w(bone) is a weighting factor to obtain a bone/calcification image, selectively and respectively for radiography and mammography, the weighting factors being adjustable, selectively so as to cause the bone structure to disappear in a resulting soft-tissue image and, alternatively, to cause the soft-tissue to disappear in a resulting bone/calcification image.

14. A digital x-ray imaging system as recited in claim 13, further comprising:
first and second, different filters selectively switched so as to be disposed between the source and the space accommodating a body, independently and respectively, for the first and second, different x-ray energy levels.

15. A digital x-ray imaging system as recited in claim 1, wherein the computer operates a computer program for decomposing the dual energy images of a body, at each pixel of the detector, into a combination of first and second different thicknesses, respectively, of first and second different phantom materials, which combination has an attenuation equivalent to an attenuation of each of the first and second, different x-ray energy levels, of a corresponding body portion as detected at the respective pixel, and for all corresponding body portions and respective pixels.

16. A digital x-ray imaging system as recited in claim 15, further comprising:
first and second, different filters selectively switched so as to be disposed between the source and the space accommodating a body, independently and respectively, for the first and second, different x-ray energy levels.

17. A digital x-ray imaging system as recited in claim 1, wherein the system further comprises:
a memory storing a predetermined calibration table of attenuation values of a combination of selected and respective, first and second thicknesses of first and second different phantom materials of respective, first and second different ranges of thicknesses, each thickness of the first phantom material being combined with each thickness of the range of thicknesses of the second phantom material and the corresponding attenuation value for each thickness of the first range, as combined with each thickness of the second range, being stored in the calibration table; and
the computer determines, from the calibration table, a combination of first and second, different respective thicknesses of the first and second, different phantom materials, which combination has an attenuation equivalent to the detected attenuation of a corresponding body portion at each pixel, and for all pixels.

18. A digital x-ray imaging system as recited in claim 17, wherein:
the computer, having decomposed all pixel values into equivalent combinations of respective first and second thicknesses of the first and second phantom materials, produces first and second phantom images, with each pixel in each image corresponding to the deduced equivalent thickness of the corresponding first and second phantom materials, and selectively recombines the first and second phantom images to produce, selectively, a soft tissue image or a bone/calcification image.

19. A digital x-ray imaging system as recited in claim 18, wherein the computer selectively recombines the first and second phantom material images, for each pixel, by weighting respective first and second counts representing the energy levels of the first and second phantom images at each pixel, and for all pixels of the detector, until the first and second images, at each pixel, have equal values and a corresponding equal appearance in a reproduced image.

20. A digital x-ray imaging system as recited in claim 1, wherein the computer operates a computer program for decomposing the dual energy images of the body, at each pixel, into an equivalent combination of respective thicknesses of first and second phantom materials, in accordance with:

$$\mu_i \cdot t_i = a_i(M2) \cdot \mu_{M1} + b_i(M2) \cdot \mu_{M2}$$

wherein:
  i denotes an ith pixel;
  $t_i$ is the thickness of the object corresponding to the ith pixel;
  M1 and M2 are first and second different phantom materials, respectively;
  $a_i$ and $b_i$ are the equivalent thicknesses of the first (M1) and second (M2) phantom materials, respectively; and
  the corresponding $\mu$'s are attenuation coefficients.

21. A digital x-ray imaging system as recited in claim 20, wherein the first (M1) and the second (M2) phantom materials are aluminum and Lucite, respectively.

22. A digital x-ray imaging system as recited in claim 21, wherein:
  for radiography the aluminum phantom is of a thickness range of 0–2 cm in steps of 0.5 mm or less and the Lucite phantom is in a thickness range of 0–30 cm in steps of 5 mm or less.

23. A digital x-ray imaging system as recited in claim 21, wherein:
  for mammography the aluminum phantom is of a thickness range of 0–5 mm in 0.2 mm steps or less and, the Lucite phantom is of a thickness range of 0–10 cm in steps of 2 mm or less.

24. A digital x-ray imaging system as recited in claim 20, wherein the computer, having decomposed all pixel values into equivalent combinations of M1 and M2 thicknesses, produces an M1 image and an M2 image, with each pixel in each image corresponding to the deduced equivalent thicknesses of the corresponding materials M1 and M2, and recombines same to produce, selectively, a soft tissue image or a bone/calcification image, in accordance with:

(Soft-tissue image)$_i = [(a:M1)_i \cdot \sin(\phi_s) + (b:M2)_i \cdot \cos((\phi_s))]$ (bone/calcification image)$_i = [(a:M1)_i \cdot \sin(\phi_b) + (b:M2)_i \cdot \cos((\phi_b))]$ wherein:
  $(M1)_i$ and $(M2)_i$ are the equivalent first and second phantom material thicknesses at the ith pixel in each decomposed image; and
  $\phi_s$ and $\phi_b$ are predefined rotation angles for obtaining, respectively and selectively, a soft-tissue image and a bone/calcification, image.

25. A digital x-ray imaging system as recited in claim 24, wherein the first (M1) and the second (M2) phantom materials are aluminum and Lucite, respectively.

26. A digital x-ray imaging system as recited in claim 25, wherein:
  for radiography, the aluminum phantom is of a thickness range of 0–2 cm in steps of 0.5 mm or less and the Lucite phantom is in a thickness range of 0–30 cm in steps of 5 mm or less.

27. A digital x-ray imaging system as recited in claim 25, wherein:
  for mammography, the aluminum phantom is of a thickness range of 0–5 mm in 0.2 mm steps or less and the Lucite phantom is of a thickness range of 0–10 cm in steps of 2 mm or less.

28. A digital x-ray imaging system as recited in claim 24, wherein:
  each of the aluminum and Lucite phantoms is of an approximately square configuration of approximately the same dimensions and are placed orthogonally with respect to each other so that x-ray energy from the source passes through each step thickness of a first phantoms and the plurality of steps of thicknesses of the second phantom, for each of the step thicknesses of the first phantom.

29. A digital x-ray imaging system as recited in claim 28, wherein each phantom has a first step of effectively 0 thickness.

30. A digital x-ray imaging system as recited in claim 24, further comprising:
  a memory storing a calibration table consisting of numbers of counts, corresponding to digital signals produced by the detector responsive to dual energy level x-ray images, for the successive steps and corresponding thicknesses of each of the first and second phantom materials.

31. A digital x-ray imaging system as recited in claim 30, wherein the computer decomposes the dual object images on a pixel-by-pixel basis into equivalent thicknesses of the first and second phantom materials using the data from the calibration table stored in the memory and a search/fit algorithm.

32. A digital x-ray imaging system as recited in claim 31, wherein the computer determines the two closest set of counts from the stored calibration table and performs a multi-parameter interpolation thereon to determine the equivalent thicknesses of the two phantom materials for each pixel.

33. A method of digital x-ray imaging, employing a x-ray source and a pixelated flat panel digital x-ray detector separated from the source by a space accommodating a body to be subjected to x-ray irradiation and imaging, comprising:
  positioning a body within the space, adjacent the detector;
  controlling the x-ray source to irradiate the body, in succession, with first and second energy level x-rays and to produce on the detector corresponding first and second x-ray images, respectively, of the first and second, different, energy levels;
  processing each of the images, on a pixel-by-pixel basis and in individual succession for all pixels, in accordance with a selected one of subtractive processing and material decomposition processing; and
  selectively displaying a soft-tissue image and a bone/calcification image.

34. A method of digital x-ray imaging as recited in claim 33, wherein the subtraction processing is performed in accordance with:

(Soft-tissue image)$_i = [(L_i)/(H_i)^{w(soft)}]$ (Bone/calcification image)$_i$=[$(L_i)/(H_i)^{w(bone)}$]

wherein:

"i" denotes the ith pixel on the pixelated flat panel digital x-ray detector,

Li and Hi represent numbers of counts corresponding to the digital signals output by the detector for the first and second energy level x-rays, respectively, for the ith pixel; and w(soft) is an adjustable weighting factor to obtain a soft-tissue image and w(bone) is a weighting factor to obtain a bone/calcification image, selectively and respectively for radiography and mammography, the weighting factors being selectively adjustable so as to cause the bone structure to disappear in a resulting soft-tissue image and, alternatively, to cause the soft-tissue to disappear in a resulting bone/calcification image.

35. A method of digital x-ray imaging as recited in claim 33, wherein the material decomposition processing further comprises:

decomposing the dual energy images of the body, at each pixel, into an equivalent combination of respective thicknesses of first and second phantom materials, in accordance with:

$$\mu_i \cdot t_i = a_i(M1) \cdot \mu_{M1} + b_i(M2) \cdot \mu_{M2}$$

wherein:

i denotes an ith pixel;

$t_i$ is the thickness of the object corresponding to the ith pixel;

M1 and M2 are first and second different phantom materials, respectively;

$a_i$ and $b_i$ are the equivalent thicknesses of the first (M1) and second (M2) phantom materials, respectively; and the corresponding $\mu$'s are attenuation coefficients.

36. A method of digital x-ray imaging as recited in claim 35, wherein the first (M1) and second (M2) phantom materials are aluminum and Lucite, respectively.

37. A method of digital x-ray imaging as recited in claim 36, wherein:

for radiography the aluminum phantom is of a thickness range of 0–2 cm in steps of 0.5 mm or less and the Lucite phantom is in a thickness range of 0–30 cm in steps of 5 mm or less.

38. A method of digital x-ray imaging as recited in claim 36, wherein:

for mammography the aluminum phantom is of a thickness range of 0–5 mm in 0.2 mm steps or less and, the Lucite phantom is of a thickness range of 0–10 cm in steps of 2 mm or less.

39. A method of digital x-ray imaging as recited in claim 35, wherein the computer, having decomposed all pixel values into equivalent combinations of M1 and M2 thicknesses, produces an M1 image and an M2 image, with each pixel in each image corresponding to the deduced equivalent thicknesses of the corresponding materials M1 and M2, and recombines same to produce, selectively, a soft tissue image or a bone/calcification image, in accordance with:

(Soft-tissue image)$_i$=[$(a{:}M1)_i \cdot \sin(\phi_s)+(b{:}M2)_i \cdot \cos((\phi_s)$]

(bone/calcification image)$_i$=[$(a{:}M1)_i \cdot \sin(\phi_b)+(b{:}M2)_i \cdot \cos((\phi_b)$]

wherein:

(M1)$_i$ and (M2)$_i$ are the equivalent first and second phantom material thicknesses at the ith pixel in each decomposed image; and $\phi_s$ and $\phi_b$ are predefined rotation angles for obtaining, respectively and selectively, a soft-tissue image and a bone/calcification, image.

40. A method of digital x-ray imaging as recited in claim 35, wherein the first (M1) and the second (M2) phantom materials are aluminum and Lucite, respectively.

41. A method of digital x-ray imaging as recited in claim 40, wherein:

for radiography, the aluminum phantom is of a thickness range of 0–2 cm in steps of 0.5 mm or less and the Lucite phantom is in a thickness range of 0–30 cm in steps of 5 mm or less.

42. A method of digital x-ray imaging as recited in claim 40, wherein:

for mammography, the aluminum phantom is of a thickness range of 0–5 mm in 0.2 mm steps or less and the Lucite phantom is of a thickness range of 0–10 cm in steps of 2 mm or less.

43. A method of digital x-ray imaging as recited in claim 39, further comprising:

storing a calibration table consisting of numbers of counts, corresponding to digital signals produced by the detector responsive to dual energy level x-ray images, for the successive steps and corresponding thicknesses of each of the first and second phantom materials.

44. A method of digital x-ray imaging as recited in claim 43, further comprising decomposing the dual object images on a pixel-by-pixel basis into equivalent thicknesses of the first and second phantom materials using the data from the calibration table stored in the memory and a search/fit algorithm.

45. A method of digital x-ray imaging as recited in claim 44, further comprising determining the two closest set of counts from the stored calibration table and performing a multi-parameter interpolation thereon to determine the equivalent thicknesses of the two phantom materials for each pixel.

46. A method of developing a calibration table for a digital x-ray imaging process, employing a pixelated flat panel digital x-ray detector separated by a space from a source of x-rays selectively switchable between first and second, different x-ray energy levels, the space accommodating a body to be subjected to x-ray irradiation and imaging, and a computer controlling the x-ray source to irradiate the body with the first and second energy level x-rays and produce corresponding first and second x-ray images respectively of the first and second, different, energy levels on the detector, comprising:

providing first and second different phantom materials of first and second different thickness ranges and assembling same in orthogonal relationship with each thickness of the first phantom material extending perpendicular to, and crossing, the range of thickness of the second phantom material;

disposing the assembled phantom materials in the space so as to be subjected to x-ray irradiation and imaging on the detector, at each of the first and second, different, energy levels;

determining, at each of first and second different energy levels, a corresponding attenuation of the irradiating x-rays energy for each pixel, and in individual succession for all pixels; and storing the attenuation levels for each combination of thicknesses of the first and second phantom materials, throughout the range of thicknesses of each, for an individual pixel and for each of the first and second, different, energy levels, in a memory.

47. A method as recited in claim 46, wherein the first and the second (M2) phantom materials are aluminum and Lucite, respectively.

48. A method as recited in claim 46, wherein:
for radiography, using a Lucite phantom in a thickness range of 0–30 cm in steps of 5 mm or less and an aluminum phantom in a thickness range of 0–2 cm in steps of 0.5 mm or less.

49. A method as recited in claim 36, wherein:
for mammography, using a Lucite phantom in a thickness range of 0–10 cm in steps of 2 mm or less and an aluminum phantom in a thickness range of 0–5 mm in steps 0.2 mm or less.

50. A method as recited in claim 47, wherein:
each of the aluminum and Lucite phantoms are each of an approximately square configuration of approximately the same dimensions and are placed orthogonally with respect to each other so that x-ray energy from the source passes through each step thickness of the first phantom and the plurality of steps of thicknesses of the second phantom, for each of the step thicknesses of the first phantom.

51. A method as recited in claim 50, wherein each phantom has a step of effectively zero thickness.

52. A digital x-ray imaging system performing subtraction processing, comprising:
a pixelated flat panel digital x-ray detector separated by a space from a source of x-rays selectively switchable between first and second, different x-ray energy levels, the space accommodating a body to be subjected to x-ray irradiation and imaging;
a computer controlling the x-ray source to irradiate the body with the first and second energy level x-rays and produce corresponding first and second x-ray images respectively of the first and second, different energy levels on the detector, the computer processing the respective digital signal outputs of the detector for the first and second digital images respectively of the first and second, different, energy levels for each pixel of the pixelated flat panel digital x-ray detector in accordance with:

(Soft-tissue image)$_i = (L_i)/(H_i)^{w(soft)}$ (Bone/calcification)$_i = (L_i)/(H_i)^{w(bone)}$ wherein:
"i" denotes the ith pixel on the pixelated flat panel digital x-ray detector,
$L_i$ and $H_i$ represent numbers of counts corresponding to the digital signals output by the detector for the first and second energy level x-rays, respectively, for the ith pixel; and
w(soft) is an adjustable weighting factor to obtain a soft-tissue image and w(bone) is a weighting factor to obtain a bone/calcification image, selectively and respectively for radiography and mammography, the weighting factors being adjustable, selectively, so as to cause the bone structure to disappear in a resulting soft-tissue image and, alternatively, to cause the soft-tissue to disappear in a resulting bone/calcification image.

53. A digital x-ray imaging system as recited in claim 52, further comprising:
first and second, different filters selectively switched so as to be disposed between the source and the space accommodating a body, independently and respectively, for the first and second, different x-ray energy levels.

54. A digital x-ray imaging system, comprising:
a pixelated flat panel digital x-ray detector separated by a space from a source of x-rays selectively switchable between first and second, different x-ray energy levels, the space accommodating a body to be subjected to x-ray irradiation and imaging;
a memory storing a predetermined calibration table of attenuation values of a combination of selected and respective, first and second thicknesses of first and second different phantom materials of respective, first and second different ranges of thicknesses, each thickness of the first phantom material being combined with each thickness of the range of thicknesses of the second phantom material and the corresponding attenuation value for each thickness of the first range, as combined with each thickness of the second range, being stored in the calibration table; and
a computer controlling the x-ray source to irradiate the body with the first and second energy level x-rays and produce corresponding first and second x-ray images respectively of the first and second, different energy levels on the detector, the computer processing the respective digital signal outputs of the detector for the first and second digital images respectively of the first and second, different, energy levels for each pixel of the pixelated flat panel digital x-ray detector, in accordance with which the computer determines, from the calibration table, a combination of first and second, different respective thicknesses of the first and second, different phantom materials, which combination has an attenuation equivalent to the detected attenuation of a corresponding body portion at each pixel, and for all pixels.

55. A digital x-ray imaging system as recited in claim 54, wherein:
the computer, having decomposed all pixel values into equivalent combinations of respective first and second thicknesses of the first and second phantom materials, produces first and second phantom images, with each pixel in each image corresponding to the deduced equivalent thickness of the corresponding first and second phantom materials, and selectively recombines the first and second phantom images to produce, selectively, a soft tissue image or a bone/calcification image.

56. A digital x-ray imaging system as recited in claim 55, wherein the computer selectively recombines the first and second phantom material images, for each pixel, by weighting respective first and second counts representing the energy levels of the first and second phantom images at each pixel, and for all pixels of the detector, until the first and second images, at each pixel, have equal values and a corresponding equal appearance in a reproduced image.

57. A digital x-ray imaging system, comprising:
a pixelated flat panel digital x-ray detector separated by a space from a source of x-rays selectively switchable between first and second, different x-ray energy levels, the space accommodating a body to be subjected to x-ray irradiation and imaging;
a computer controlling the x-ray source to irradiate the body with the first and second energy level x-rays and produce corresponding first and second x-ray images respectively of the first and second, different energy levels on the detector, the computer processing the respective digital signal outputs of the detector for the first and second digital images respectively of the first and second, different, energy levels for each pixel of the pixelated flat panel digital x-ray detector, wherein:

the computer operates a computer program for decomposing the dual energy images of the body, at each pixel, into an equivalent combination of respective thicknesses of first and second phantom materials, in accordance with:

$$\mu_i \cdot t_i = a_i(M1) \cdot \mu_{M1} + b_i(M2) \cdot \mu_{M2}$$

wherein:

i denotes an ith pixel;

$t_i$ is the thickness of the object corresponding to the ith pixel;

M1 and M2 are first and second different phantom materials, respectively;

$a_i$ and $b_i$ are the equivalent thicknesses of the first (M1) and second (M2) phantom materials, respectively; and the corresponding $\mu$'s are attenuation coefficients.

58. A digital x-ray imaging system as recited in claim 57, wherein the first (M1) and the second (M2) phantom materials are aluminum and lucite, respectively.

59. A digital x-ray imaging system as recited in claim 58, wherein:

for radiography, the aluminum phantom is of a thickness range of 0–2 cm in steps of 0.5 mm or less and the lucite phantom is in a thickness range of 0–30 cm in steps of 5 mm or less.

60. A digital x-ray imaging system as recited in claim 58, wherein:

for mammography, the aluminum phantom is of a thickness range of 0–5 mm in 0.2 mm steps or less and, the lucite phantom is of a thickness range of 0–10 cm in steps of 2 mm or less.

61. A digital x-ray imaging system as recited in claim 57, wherein the computer, having decomposed all pixel values into equivalent combinations of M1 and M2 thicknesses, produces an M1 image and an M2 image, with each pixel in each image corresponding to the deduced equivalent thicknesses of the corresponding materials M1 and M2, and recombines same to produce, selectively, a soft tissue image or a bone/calcification image, in accordance with:

$$\text{(Soft-tissue image)}_i = [(a:M1)_i \cdot \sin(\phi_s) + (b:M2)_i \cdot \cos((\phi_s)]$$

$$\text{(bone/calcification image)}_i = [(a:M1)_i \cdot \sin(\phi_b) + (b:M2)_i \cdot \cos((\phi_b)]$$

wherein:

$(M1)_I$ and $(M2)_i$ are the equivalent first and second phantom material thicknesses at the ith pixel in each decomposed image; and $\phi_s$ and $\phi_b$ are predefined rotation angles for obtaining, respectively and selectively, a soft-tissue image and a bone/calcification, image.

62. A method of digital x-ray imaging, employing a x-ray source and a pixelated flat panel digital x-ray detector separated from the source by a space accommodating a body to be subjected to x-ray irradiation and imaging, comprising:

positioning a body within the space, adjacent the detector;

controlling the x-ray source to irradiate the body, in succession, with first and second energy level x-rays and to produce on the detector corresponding first and second x-ray images, respectively, of the first and second, different, energy levels;

processing each of the images, on a pixel-by-pixel basis and in individual succession for all pixels, in accordance with in accordance with:

$$\text{(Soft-tissue image)}_i = [(L_i)/(H_i)^{w(soft)}]$$

$$\text{(Bone/calcification image)}_i = [(L_i)/(H_i)^{w(bone)}]$$

wherein:

"i" denotes the ith pixel on the pixelated flat panel digital x-ray detector,

Li and Hi represent numbers of counts corresponding to the digital signals output by the detector for the first and second energy level x-rays, respectively, for the ith pixel; and w(soft) is an adjustable weighting factor to obtain a soft-tissue image and w(bone) is a weighting factor to obtain a bone/calcification image, selectively and respectively for radiography and mammography, the weighting factors being selectively adjustable so as to cause the bone structure to disappear in a resulting soft-tissue image and, alternatively, to cause the soft-tissue to disappear in a resulting bone/calcification image.

63. A method of digital x-ray imaging as recited in claim 62, wherein the material decomposition processing further comprises:

decomposing the dual energy images of the body, at each pixel, into an equivalent combination of respective thicknesses of first and second phantom materials, in accordance with:

$$\mu_i \cdot t_i = a_i(M1) \cdot \mu_{M1} + b_i(M2) \cdot \mu_{M2}$$

wherein:

i denotes an ith pixel;

$t_i$ is the thickness of the object corresponding to the ith pixel;

M1 and M2 are first and second different phantom materials, respectively;

$a_i$ and $b_i$ are the equivalent thicknesses of the first (M1) and second (M2) phantom materials, respectively; and the corresponding $\mu$'s are attenuation coefficients.

64. A method of digital x-ray imaging as recited in claim 63, wherein the computer, having decomposed all pixel values into equivalent combinations of M1 and M2 thicknesses, produces an M1 image and an M2 image, with each pixel in each image corresponding to the deduced equivalent thicknesses of the corresponding materials M1 and M2, and recombines same to produce, selectively, a soft tissue image or a bone/calcification image, in accordance with:

$$\text{(Soft-tissue image)}_i = [(a:M1)_i \cdot \sin(\phi_s) + (b:M2)_i \cdot \cos((\phi_s)]$$

$$\text{(bone/calcification image)}_i = [(a:M1)_i \cdot \sin(\phi_b) + (b:M2)_i \cdot \cos((\phi_b)]$$

wherein:

$(M)_I$ and $(M2)_i$ are the equivalent first and second phantom material thicknesses at the ith pixel in each decomposed image; and $\phi_s$ and $\phi_b$ are predefined rotation angles for obtaining, respectively and selectively, a soft-tissue image and a bone/calcification, image.

* * * * *